(12) United States Patent
Sandstedt

(10) Patent No.: US 8,926,541 B1
(45) Date of Patent: Jan. 6, 2015

(54) MEANS TO REMOVE BLOOD STREAM DEPOSITS FROM A BODY

(76) Inventor: Gary O. Sandstedt, Saint Louis, MO (US)

( * ) Notice: Subject to any disclaimer, the term of this patent is extended or adjusted under 35 U.S.C. 154(b) by 315 days.

(21) Appl. No.: 13/374,655

(22) Filed: Jan. 6, 2012

(51) Int. Cl.
*A61M 37/00* (2006.01)

(52) U.S. Cl.
USPC ........ 604/5.01; 604/5.02; 604/5.03; 604/5.04

(58) Field of Classification Search
CPC ....... A61M 1/3624; A61M 1/34; A61M 1/16; A61M 1/3639; A61M 1/3621; A61M 1/3693; A61M 2001/3696; A61M 2205/12; A61M 2001/303
USPC .................................................. 604/4.01–6.16
See application file for complete search history.

(56) References Cited

U.S. PATENT DOCUMENTS

| 7,066,900 B2 * | 6/2006 | Botto et al. ................... 604/6.08 |
| 8,075,611 B2 | 12/2011 | Millwee et al. |
| 8,080,052 B2 | 12/2011 | Burgermeister et al. |

* cited by examiner

*Primary Examiner* — Philip R Wiest

(57) ABSTRACT

This invention relates to a means of clearing out a cholesterol, calcium and plaque build-up resident to a living circulatory system, in addition to dissolving various kinds of blood clots, and removing other foreign matter, all by means of charged particle migration, through the application of an electromotive source.

20 Claims, 3 Drawing Sheets

MEANS TO REMOVE BLOOD STREAM DEPOSITS FROM A BODY

BACKGROUND OF THIS INVENTION

The clogging of the cardiovascular system with the build-up of cholesterol, calcium, and the formation of blood clots, is a major health hazard; often leading to heart attacks, strokes, and the loss of circulation to, and in, vital organs and body extremities, resulting in death.

The means of treating and controlling the effects of those substances has been intensified in recent years with the introduction of cholesterol lowering drugs, the use of blood thinners, and the implementation of various surgical procedures.

PRIOR ART DISCUSSION

One surgical procedure to fight the build-up of cholesterol is through the use of stents to prop open arteries and by vein transplants, to bypass diseased arteries.

Another surgical procedure is frequently required to replace heart valves, due to an inhibiting build-up of calcium deposits.

Blood clots and foreign matter that can't be dissolved by medication, and inhibit blood flow, threatening heart attacks and strokes, are controlled through the use of stents, or by other surgical procedures.

FIELD OF INVENTION

This invention addresses a unique means of treatment, designed to clear out the cardiovascular system of a cholesterol, calcium, and plaque build-up of various types, in addition to eliminating various kinds of blood clots, all through the process of charged particle migration.

OBJECTS OF THIS INVENTION

1. To provide both a permanent and on-going protection against a cholesterol, calcium, plaque and other foreign substance build-up, accumulated in a circulatory system.
2. To provide both a permanent and on-going protection against various kinds of circulatory system blood clots.
3. To eliminate the need for stents, bypasses, and cardiovascular medications.

PRIOR ART REFERENCES CITED

U.S. Patent Documents U.S. Pat. Nos. 8,075,611 8,080,052

Patent document U.S. Pat. No. 8,075,611 reveals a surgical sutureless heart valve attached to a stent frame for delivery to a location in a patient using percutaneous implantation devices and methods.

Patent document U.S. Pat. No. 8,080,052 reveals a stent in the form of a multi-cellular tubular structure, which provides for increased flexibility during delivery and enhanced conformability to the shape of a curved artery.

The prior referenced art reveals cardiovascular obstruction accommodation, as opposed to cardiovascular obstruction elimination, which is the subject of this invention.

IN SUMMATION

Prior art does not disclose the system of this invention, which encompasses a unique process of pre-emptive control and elimination of a cholesterol, calcium, plaque and other forms of build-up in the circulatory system; and in the elimination of various kinds of circulatory system blood clots.

DESCRIPTION OF AN EMBODIMENT

Figure 1:
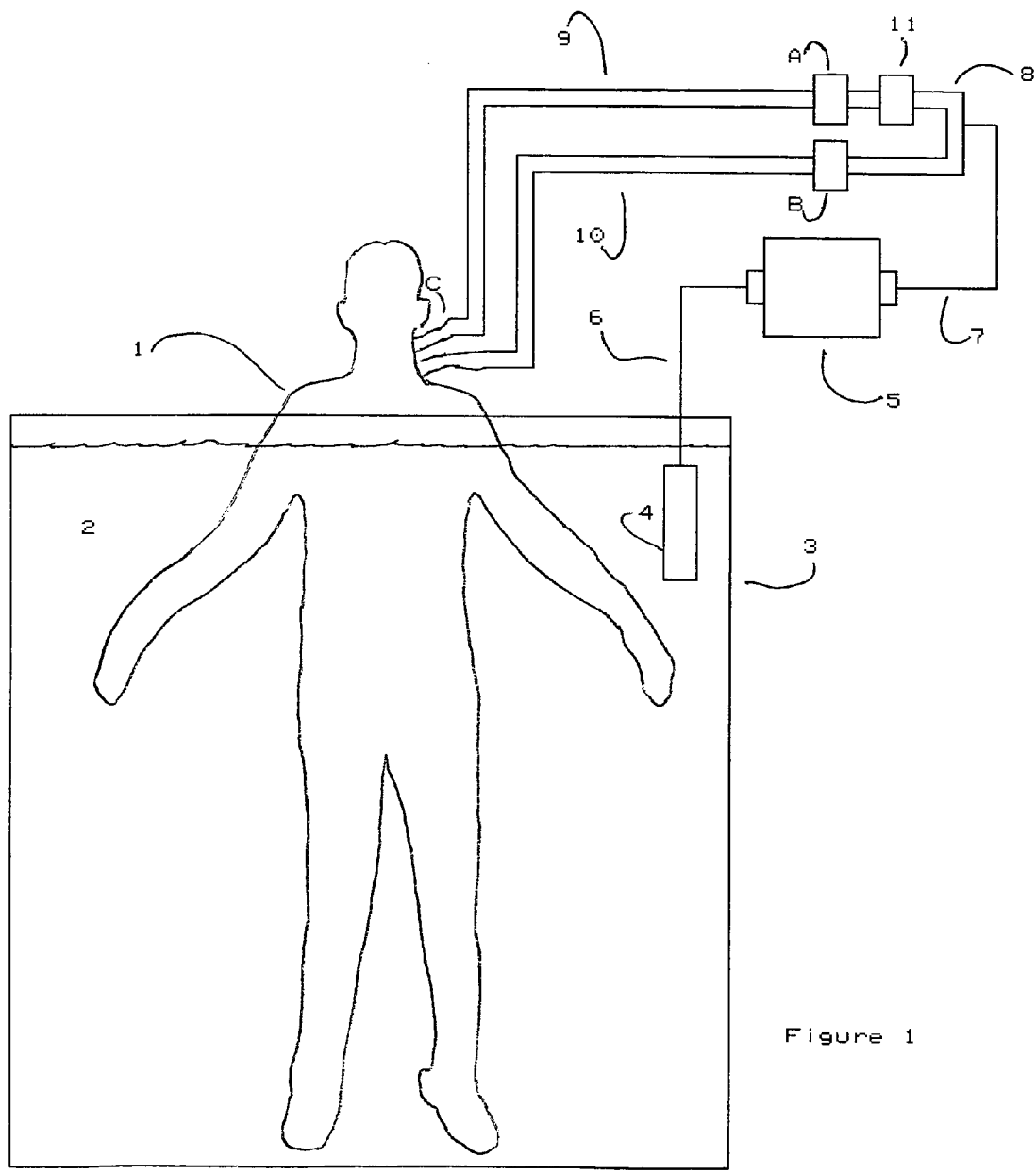
FIG. 1, profiles body 1, immersed in ionized current carrying solution 2, of vat 3, with attached treatment peripherals.

FIG. 1, shows a profile of body 1, immersed in ionized current carrying solution 2, of vat 3.

Also immersed in ionized current carrying solution 2, of vat 3, is circuit electrode 4.

Circuit electrode 4, is connected through electrical conductor 6, to a specific polarity terminal of electromotive source 5.

Electrically conductive shunt pipe 8, is connected through electrical conductor 7, to the specific opposite polarity terminal of electromotive source 5.

Interceding artery C, of body 1, is connecting, electrically non-conductive blood carrying input conduit 9, and electrically non-conductive blood carrying output conduit 10, attached to respective ports A, and B, of electrically conductive shunt pipe 8, with filter 11.

This configuration places body 1, at one electrical polarity potential and electrically conductive shunt pipe 8, at an opposite, opposing electrical polarity potential.

The resulting arrangement allows for the circulating blood of body 1, to assume an electrically charged polarity potential opposite that of the entire body 1, immersed in ionized current carrying solution 2, of vat 3.

Therefore, particles of cholesterol, calcium, plaque and other foreign substance deposited in the circulatory system of the charged body 1, will be drawn into liquid suspension by the oppositely charged continuous blood flow through the circulatory system of body 1.

Additionally, various kinds of blood clots resident in the circulatory system of body 1, will be disassembled into suspension, particle by particle, by the oppositely charged continuous flow of blood.

Example

Body 1, immersed in ionized current carrying solution 2, of vat 3, is negatively charged through contact with the negative terminal of electromotive source 5, by means of electrical conductor 6, and electrode 4, which is similarly immersed in ionized current carrying solution 2, of vat 3, to complete the negative current flow path.

Interceding bisected artery "C", of body 1, are connecting, electrically non-conductive blood carrying conduits 9, and 10, attached to electrically conductive shunt pipe 8, at junctures A, and B, respectively, to close the blood flow (loop) circuit between body 1, circulating blood, and electrically conductive shunt pipe 8.

Attached to electrically conductive shunt pipe 8, is the positive terminal of electromotive source 5, through electrical conductor 7, to complete the positive current flow path.

Therefore with body 1, blood positively charged by virtue of passing though positively charged electrically conductive shunt pipe 8, and the whole of body 1, being negatively charged by being immersed in ionized current carrying solution 2, of vat 3; negatively charged cholesterol, calcium, plaque and other particles, are attracted away from the walls of body 1, circulatory system, by the flow of positively charged blood, and drawn into suspension, particle by particle, for eventual elimination from the circulatory system.

Filter 11, of electrically conductive shunt pipe 8, collects the negatively charged residue, loosened from the walls of body 1, circulatory system, by the attraction of the positively charged, circulating blood.

Similarly, blood clots are disassembled and removed from the circulatory system also by filter 11.

Figure 2:
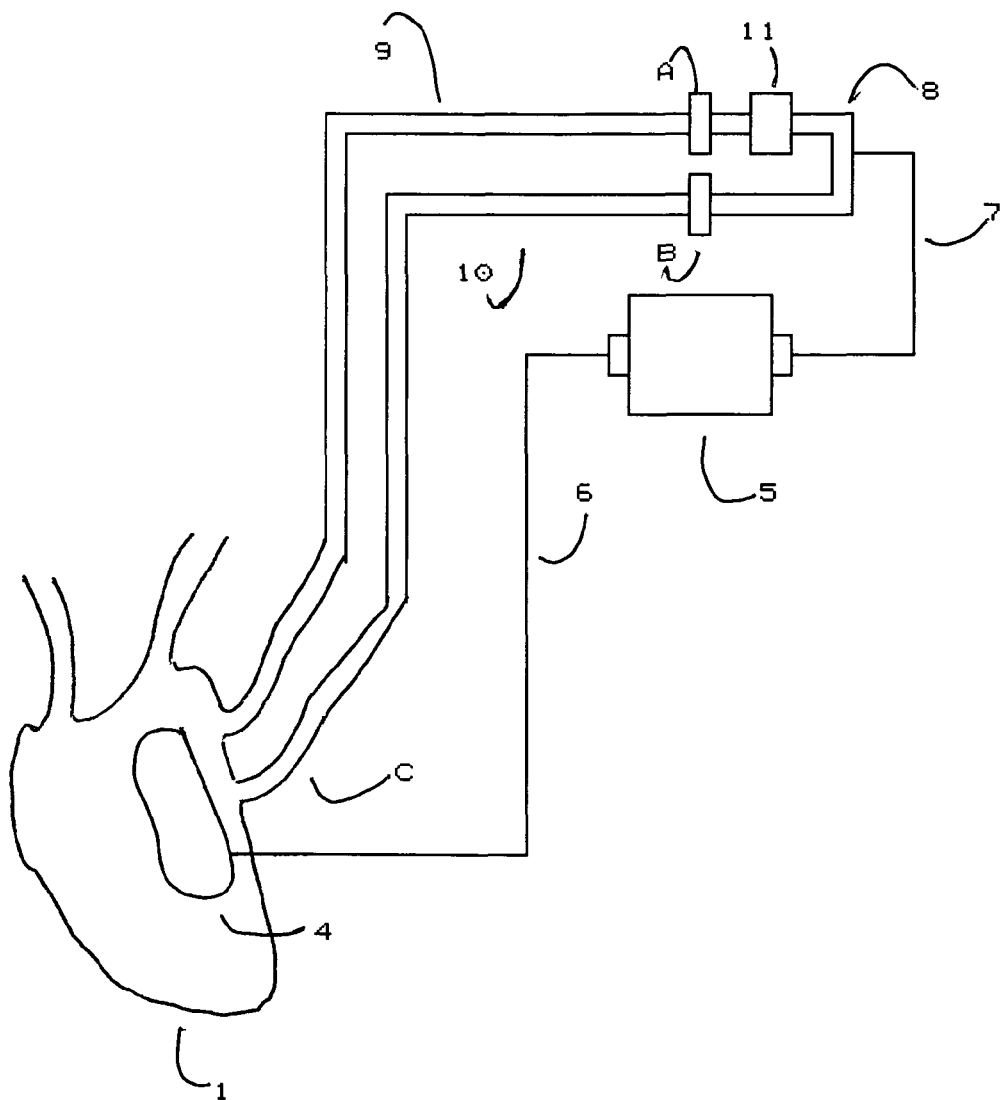
FIG. 2, represents heart 1, configured for a topical treatment of a circulatory obstruction.

FIG. 2, shows heart 1, configured for a topical treatment of a circulatory obstruction.

Placed on the target area of an obstructed artery of heart 1, is electrically conductive appliance 4, with an electrical potential of a certain polarity applied from electromotive source 5, through electrical conductor 6.

Electrically conductive shunt pipe 8, has two ports, A, and B, through which blood passes from one end to the other, when placed in operation.

Interceding bisected artery "C", of heart 1, are connecting, non-conductive blood carrying conduits 9, and 10, attached to electrically conductive shunt pipe 8, at junctures A, and B, respectively, to close the circuit loop between heart 1, and electrically conductive shunt pipe 8.

Electrically conductive shunt pipe 8, is connected through electrical conductor 7, to the opposite polarity terminal of electromotive source 5.

This configuration places the target area of heart 1, at one electrical polarity potential and electrically conductive shunt pipe 8, at an opposite, opposing electrical polarity potential.

Example

Electrically conductive appliance 4, is negatively charged through contact with the negative terminal of electromotive source 5, by means of electrical conductor 6, completing the negative current flow path.

Attached to electrically conductive shunt pipe 8, is the positive terminal of electromotive source 5, through electrical conductor 7, completing the positive current flow path.

With heart 1, blood positively charged by virtue of passing though positively charged electrically conductive shunt pipe 8, and the treatment area of heart 1, negatively charged by treatment appliance 4; negatively charged particles of cholesterol, calcium and plaque lining the walls of heart 1, circulatory system, target area, are attracted away by the continuous flow of oppositely charged blood through the circulatory system of heart 1.

Additionally, various kinds of blood clots in the targeted area of the circulatory system of heart 1, will also be disassembled, particle by particle, by the circulating blood flow through heart 1.

The particles of disassembled deposits of cholesterol, calcium, plaque and blood clots are rendered into free suspension, and subsequently removed from the circulatory system blood flow by filter 11.

Figure 3:
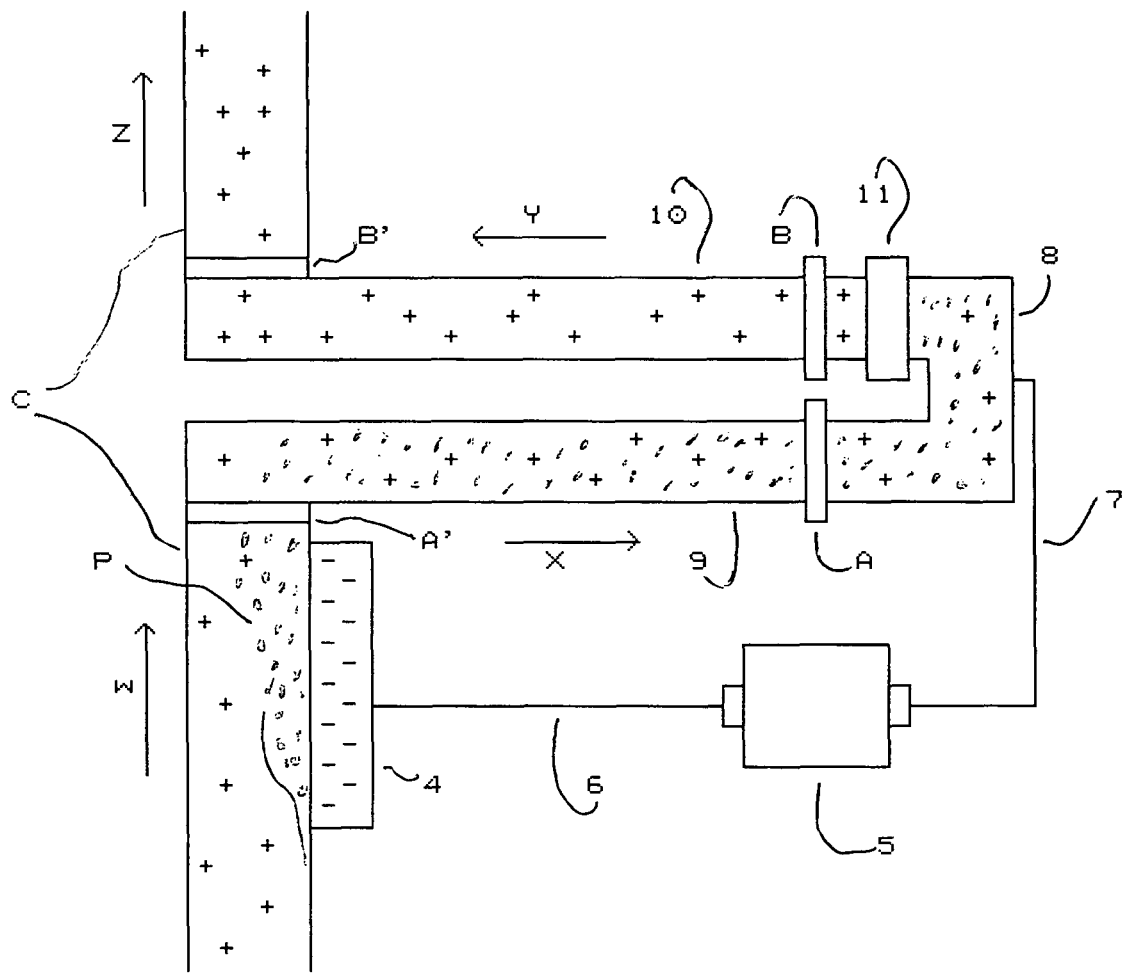
FIG. 3, is a detailed representative view of bisected artery C, with attached treatment peripherals.

FIG. 3, shows an enlarged view of bisected artery C, interceded at junctures A', and B', by respective electrically non-conductive conduits 9, and 10, which complete a closed circuit blood flow by their connection to shunt 8, at respective junctures A, and B.

Connected to shunt 8, is the positive terminal of electromotive source 5, through electrical conductor 7.

Blood circulating through artery C, electrically non-conductive conduits 9, 10, and filter 11, assumes a positive electrical charge by continuous contact with shunt 8, with arrows W, X, Y, and Z, indicating the flow pattern.

Connected to the negative terminal of electromotive source 5, through electrical conductor 6, is negatively charged topical application appliance 4, contacting the exterior of artery C.

Also shown resident in artery C, are substance particles P, negatively charged by applied appliance 4.

Negatively charged substance particles P, are being continuously eroded away, swept into the flow of positively charged circulating blood, and subsequently removed from the blood stream by filter 11.

SUMMARY OF THIS INVENTION

This invention uses an electrically charged blood stream to attract away and remove the cholesterol, calcium, plaque and other forms of build-up, residing in the circulatory system of a body, or a component of a body, in addition to various kinds of blood clots.

IN CONCLUSION

The implementation of concepts described and depicted herein, are just one example of several means to accomplish the end results claimed for this invention.

What is claimed is:

1. A procedure in which a living cardiovascular system is purged of foreign substance, by routing blood flow through an electrically charged shunt configuration, comprising a connecting electrically insulated input conduit and a connecting electrically insulated output conduit, to form a closed circuit loop, with blood flow assuming a certain polarity electrical charge, derived by shunt contact with an electromotive source, through a conductor; and body tissue of the living circulatory system assuming a certain opposite polarity electrical charge, derived by an application appliance contact with an electromotive source, through a conductor; with each polarity derived from a common electromotive source, producing one polarity potential of circulating blood, attracting away oppositely charged particles of substance deposited on the circulatory system walls of the subject, by charged particle migration; to be rendered free-standing in the blood stream, and subsequently removed from the flow by filtration.

2. The invention of claim 1, comprising applying an active mechanism of charged particle migration, with circulating blood serving as the migratory medium.

3. The invention of claim 1, comprising topical substance removal from the walls of a circulatory system, by placement on the target area of a subject, an appliance, whose charge is opposite that of the circulating blood.

4. The invention of claim 1, comprising using the electrically charged shunt, interceding a living circulatory blood flow, to form a closed circuit loop, whose body tissue, oppositely charged through submersion in a vat containing an electrically conductive solution, produces a contentious electrical potential to facilitate charged particle migration, by means of an electron flow, to erode away substance lining the walls of a living circulatory system, for elimination by filtering the blood stream.

5. The invention of claim 1, comprising removal of foreign substance from a living circulatory system by electrically charged particles of a specific polarity drawn into liquid suspension by an electrically charged blood flow of the opposite polarity.

6. The invention of claim 1, comprising removal of at least one cholesterol particle from a living circulatory system by charged particle migration.

7. The invention of claim 1, comprising removal of at least one calcium particle from a living circulatory system by charged particle migration.

8. The invention of claim 1, comprising removal of at least one blood clot particle from a living circulatory system by charged particle migration.

9. The invention of claim 1, wherein the appliance is copper based and topically placed.

10. The invention of claim 1, wherein the appliance is zinc based and topically placed.

11. The invention of claim 1, wherein the shunt is copper based.

12. The invention of claim 1, wherein the shunt is zinc based.

13. The invention of claim 1, comprising providing an electrical source in the presence of fluids to remove at least one cholesterol particle from the walls of a living circulatory system, into liquid suspension through charged particle migration.

14. The invention of claim 1, comprising providing an electrical source in the presence of fluids to remove at least one calcium particle from the walls of a living circulatory system, into liquid suspension through means of charged particle migration.

15. The invention of claim 1, comprising providing an electrical source in the presence of fluids to remove at least one blood clot particle from a body circulatory system, into liquid suspension through means of charged particle migration.

16. The invention of claim 1, comprising moving at least one particle of plaque tissue into liquid suspension, for elimination, through means of charged particle migration.

17. The invention of claim 1, comprising the introduction of at least one free ion by an external electromotive source to effect the migration of at least one particle of organic tissue in a living organism into liquid suspension for elimination.

18. The invention of claim 1, wherein at least one particle of deposited substance is separated from live tissue by means of charged particle migration.

19. The invention of claim 1, wherein at least one foreign circulatory substance is moved by charged particle migration to a state of free suspension, in circulating blood, for elimination by means of filtration.

20. The invention of claim 1, comprising charged particle migration by artificial polarization of living tissue through the application of an electromotive source.

* * * * *